United States Patent [19]

Barnette et al.

[11] 4,339,395

[45] Jul. 13, 1982

[54] TREATMENT OF OLEFIN HYDROCYANATION PRODUCTS

[75] Inventors: Willie J. Barnette; Farland E. Henry; Morris Rapoport, all of Orange, Tex.

[73] Assignee: E. I. Du Pont de Nemours and Company, Wilmington, Del.

[21] Appl. No.: 254,487

[22] Filed: Apr. 15, 1981

[51] Int. Cl.³ .................. C07C 120/00; C07C 121/20
[52] U.S. Cl. .............................................. 260/465.8 R
[58] Field of Search ................................ 260/465.8 R

[56] References Cited

U.S. PATENT DOCUMENTS

| | | | |
|---|---|---|---|
| 3,496,218 | 2/1970 | Drinkard, Jr. et al. | 260/465.8 R |
| 3,766,237 | 10/1973 | Chia et al. | 260/464 X |
| 3,766,241 | 10/1973 | Drinkard, Jr. | 260/465.8 R |
| 3,773,809 | 11/1973 | Walter | 260/465.8 R |
| 3,903,120 | 9/1975 | Shook, Jr. et al. | 260/465.3 X |
| 4,080,374 | 3/1978 | Corn | 260/465.8 R X |
| 4,082,811 | 4/1978 | Shook, Jr. | 260/465.8 R X |

*Primary Examiner*—Joseph Paul Brust

[57] ABSTRACT

Use of ammonia to control interfacial rag formation when olefin hydrocyanation products are contacted with a hydrocarbon.

4 Claims, No Drawings

TREATMENT OF OLEFIN HYDROCYANATION PRODUCTS

BACKGROUND OF THE INVENTION

1. Field of the Invention

The present invention relates to the recovery of catalyst components and, more particularly, to a process for the recovery of zero-valent nickel complexes from the stream obtained by the hydrocyanation of olefins, e.g., from the preparation of adiponitrile by hydrocyanation of butadiene using nickel complexes as catalysts with triarylboranes, e.g., triphenylborane as the catalyst promoters.

2. Description of the Prior Art

The hydrocyanation process to which the present invention is particularly applicable is described in U.S. Pat. No. 3,496,218 issued on Feb. 17, 1970. Catalyst used in the process is zero-valent nickel; a particular form of which is described in U.S. Pat. No. 3,766,237 issued on Oct. 16, 1973.

U.S. Pat. No. 4,082,811 issued on Apr. 4, 1978 discloses a hydrocyanation process coupled with a method for recovery of the catalyst. The particular operation to which the present invention is applied is found in column 2, lines 39–42 of this patent.

The feasibility of extracting nickel catalyst mixture from dinitriles and specifically from adiponitrile is discussed in detail in U.S. Pat. No. 3,773,809 issued on Nov. 20, 1973. This patent discloses several organics which may be employed in the extraction process along with detailed analyses of the phases which are obtained upon extraction. In column 4, lines 3–15 the use of an arylborane compound as a catalyst promoter is disclosed.

SUMMARY OF THE INVENTION

In a process for the production of dinitriles, e.g., adiponitrile, by the hydrocyanation of nonconjugated, ethylenically unsaturated organic nitriles having 4–20 carbon atoms, e.g., 3- and/or 4-pentenenitriles in the presence of a zero-valent nickel catalyst promoted with an organoborane, e.g., triphenylborane and containing excess neutral ligand to produce a reaction product comprising unreacted nitriles, dinitriles, catalyst, neutral ligand and deactivated catalyst wherein the reaction product is contacted with an aliphatic or alicyclic hydrocarbon, the improvement which comprises injecting at least about 150 parts per million of essentially water-free ammonia into said reaction product before the reaction product is contacted with said hydrocarbon.

DETAILED DESCRIPTION OF THE INVENTION

The prior art referred to hereinabove describes hydrocyanation processes to which the present invention is applicable. Specifically this invention applies to the treatment of the hydrocyanation product with an aliphatic or alicyclic hydrocarbon to recover catalyst from mono- and dinitriles as described in U.S. Pat. No. 4,082,811, e.g., in column 2, lines 23–42 and in U.S. Pat. No. 3,773,809 which disclosures are incorporated herein by this reference. In all instances a substantial portion, e.g., 50% to 95% of the volatile components of the reaction product, e.g., unreacted mononitriles are removed, e.g., by flash distillation before the stream is contacted with the hydrocarbon. The stream which after removal of volatile components is contacted with an aliphatic or alicyclic hydrocarbon can be obtained from the hydrocyanation of any nonconjugated, ethylenically unsaturated organic nitrile of from 4 to 20 carbon atoms. Of particular interest is the hydrocyanation of pentenenitriles, e.g., cis- and trans-3-pentenenitrile (3-PN's), 4-pentenenitrile (4-PN) and mixtures thereof (3,4-PN's) to produce adiponitrile (ADN) which is an intermediate used in the production of hexamethylenediamine. This diamine is used to produce polyhexamethyleneadipamide, a commercial polyamide useful in forming fibers, films and molded articles.

Typically, the catalyst which is employed in the hydrocyanation is a zero-valent nickel ($Ni^0$) catalyst prepared according to U.S. Pat. No. 3,903,120 issued on Sept. 2, 1975. Of particular interest is catalyst having the general formula $NiL_4$ where L is a neutral ligand such as a triarylphosphite of the formula $P(OAr)_3$ wherein Ar is an aryl group of up to 18 carbon atoms. Illustrative of the aryl groups are methoxyphenyl, tolyl, xylyl and phenyl. Meta- and para-tolyl and mixtures thereof are the preferred aryl groups. Usually excess ligand is employed.

The promoters which are used with the above described catalyst are triarylboranes including those of the formula $BR_3$ wherein R is an aryl or substituted aryl group having 6 to 12 carbon atoms, e.g., phenyl, ortho-tolyl, para-tolyl, napthyl, methoxyphenyl, biphenyl, chlorophenyl and bromophenyl. Triphenylborane (TPB) is preferred.

A representative analysis of a hydrocyanation reaction product before removal of volatiles and showing the ranges of concentrations of the components is given in Table I. The concentrations will vary according to reaction conditions.

TABLE I

| Compound | Amount (% by weight) |
|---|---|
| Neutral Ligand (L) | 15–35 |
| 3,4-PN's | 20–60 |
| Adiponitrile (ADN) | 15–50 |
| Other Dinitriles | <3 |
| Soluble Catalyst and Promoter ($Ni^0$-$BR_3$) | <1 |
| Solids* | 0.1–4 |
| Other Organics | 4–8 |

*Generally as defined in U.S. Pat. No. 4,082,811 at column 3, lines 55–60.

Usually at least 50–95% of the mononitriles present in the product are removed by methods obvious to those skilled in the art, e.g., by flash distillation to permit the formation of two liquid phases when the product is contacted with the hydrocarbon. Suitable hydrocarbons include paraffins and cycloparaffins (aliphatic and alicyclic hydrocarbons) having a boiling point in the range of about 30° C. to about 135° C. including n-pentane, n-hexane, n-heptane and n-octane as well as the corresponding branched chain paraffinic hydrocarbons having a boiling point within the range specified. Useful alicyclic hydrocarbons include cyclopentane, cyclohexane and cycloheptane as well as alkyl substituted alicyclic hydrocarbons having a boiling point within the specified range. Mixtures of hydrocarbons may also be used such as, for example, mixtures of the hydrocarbons noted above or commercial heptane which contains a number of hydrocarbons in addition to n-heptane. Cyclohexane is the preferred solvent.

The lighter (hydrocarbon) phase is directed to suitable equipment to recover catalyst, reactants, etc. for recycle to the hydrocyanation while the heavier (lower) phase containing principally dinitriles is directed to product recovery after removal of the solids which accumulate in the heavier phase. These solids contain valuable components which are also recovered, e.g., by the process set forth in U.S. Pat. No. 4,082,811.

It has been discovered that during extended periods of continuous extraction a minor amount of the solids tends to collect at the interface between the two liquid phases and coat the heavy liquid droplets passing from the lighter to the heavier phase eventually resulting in the formation of a cellular mixture of globules which are coated with these solids. The solids, when dried, are a grey powder of 0.1–20 micron particle size and can contain about 0.1–3% boron. It is believed that their chemical composition is quite similar to the solids described in U.S. Pat. No. 4,082,811 (see Table I of the patent). This cellular mixture, or interfacial rag, hinders, if not halts, the phase separation. This rag must be removed from the interface as it accumulates if phase separation is to be conducted continuously.

It has been discovered that the presence of minor amounts of substantially water-free ammonia will cause a breakdown of the rag or at least retard its formation to the extent that effective phase separation is realized on a continuous basis. At least about 150 and preferably, at least 200 parts per million by weight of ammonia based upon the weight of the reaction product is required to achieve this result. Although the upper limit of the amount of ammonia employed is not critical and, indeed, sufficient ammonia can be added to dissolve the solids, it is generally unnecessary to introduce more than about 500 ppm of ammonia to eliminate or at least control rag formation.

The presence of water in the hydrocyanation system is undesirable and for this reason the ammonia should be water free, i.e., contain less than 0.3% water based upon the weight of ammonia. Commercially available anhydrous ammonia is quite satisfactory. The form in which the ammonia is introduced is not critical.

The temperature of the stream into which the ammonia is introduced can vary over a wide range but usually it is convenient to maintain the temperature in the range of about 25°–80° C. Methods to obtain adequate contact of the ammonia with the stream are apparent to those skilled in the art.

The following examples and comparatives are presented to illustrate but not to restrict the present invention. Parts and percentages are by weight unless otherwise noted.

EXAMPLES 1 AND 2 AND COMPARATIVES

The following abbreviations and definitions are used herein:

TTP = the reaction product of $PCl_3$ and commercially available m,p-cresol which contains minor amounts of related phenols.

$$\text{Conversion} = \frac{\text{mols of 3- and 4-PN's consumed}}{\text{mols of 3- and 4-PN's fed}} \times 100$$

$$\text{Yield (ADN)} = \frac{\text{mols of ADN produced}}{\text{mols of 3- and 4-PN's consumed}} \times 100$$

$$\text{Yield (2PN)} = \frac{\text{mols of 2-PN produced}}{\text{mols of 3- and 4-PN's consumed}} \times 100$$

The apparatus employed comprises 3 glass flasks as reactors of approximately 25 cc in volume which were connected in series with the overflow from the first reactor directed by gravity to the second reactor and the overflow from the second reactor directed by gravity to the third reactor. Overflow from the last reactor is retained in a product receiver which is periodically changed. Each reactor is equipped with an individually controlled electrical heating means and side arms for sampling the contents during the course of a run. The first reactor is provided with an inlet port for catalyst solution, promoter solution and pentenenitriles. Each reactor is also equipped with a port for introductions of hydrogen cyanide below the liquid contents of the flasks. A nitrogen inlet is provided to the vapor space of each reactor and the product receiver to provide a non-oxidizing atmosphere. The pentenenitriles which are introduced to the reactor and are used to prepare the solutions described hereinbelow contains about 98% 3PN and 1% 4PN with trace amounts of other nitriles. Pentenenitriles of lesser purity can be employed with essentially similar results. Catalyst solution which is introduced into the first reactor is prepared by reacting a mixture containing 77% TTP, 20% PN's, 3% nickel powder, to which mixture is added 100 ppm chloride catalyst as phosphorous trichloride. The mixture is heated for 16 hours at 80° C., cooled and filtered to yield a solution containing approximately 2.7% by weight zero-valent nickel ($Ni^0$). The promoter solution is prepared by dissolving a mixture of dry TPB in the above described nitriles to yield a solution containing about 20% by weight triphenylborane. Hydrogen cyanide employed in the examples is essentially free of sulfuric acid and contains only trace amounts of sulfur dioxide. The hydrogen cyanide is cooled to about 0° C. to prevent degradation prior to introduction. The system is started up by adding catalyst solution, pentenenitriles and promoter solution to each reactor at room temperature. Agitation is then started. After warming the reactors to 60° C. introduction of hydrogen cyanide, catalyst and promoter solutions and pentenenitriles is commenced and regulated to achieve an overall ratio of hydrogen cyanide to $Ni^0$, TPB, TTP, 3,4-PN's of 25.0, 390.7, 2.90, and 0.192 respectively. Approximately 0.378 weight percent $Ni^0$ is present in the ingredients as fed. ADN is produced at a rate of 3.43 grams/cc/min $\times 10^{-4}$. The product contains 58.4 weight percent 3,4-PN's; the conversion to ADN is 20% and the yield to ADN is 87.4 The yield to 2-PN is 8.4%.

The reaction product is collected and then distilled under vacuum to remove a major portion of unreacted mononitriles. It has the analysis set forth in Table II.

TABLE II

| Compound | Amounts (% by weight) |
| --- | --- |
| Neutral Ligand (TTP) | 44.2 |
| 3,4-PN's | 7.5 |
| ADN | 37.9 |
| Other Dinitriles | <3 |
| Other Organics | <1 |
| Soluble Catalyst and Promoter (as $Ni^0$ and TPB) | <1 |
| Solids* | <1 |

*Generally as defined in U.S. Pat. No. 4,082,811 at column 3, lines 55–60.

Anhyrous ammonia gas at 25° C. is added to five portions of the above reaction product by injecting a measured quantity of ammonia into the product in the amount indicated in Table III. One portion is not treated. Approximately 20 ml of each portion is introduced into a 50 ml graduated cylinder along with 25 ml of reagent grade cyclohexane. The cylinders are closed, heated to 60° C. and inverted fifteen times following which the phases are permitted to disengage at 60° C. The results are shown in Table III. It is noted that as the amount of ammonia is increased, there is an increased tendency for the solids to migrate to the lower phase.

TABLE III

| Comparative | Added Ammonia (ppm) | Interfacial Rag (% By Volume) |
|---|---|---|
| A | 0 | 9% |
| B | 25 | 9% |
| C | 50 | 8% |
| D | 100 | 8% |
| Example | | |
| I | 200 | 0% |
| II | 500 | 0% |

We claim:

1. In a process for the production of dinitriles by the addition of hydrogen cyanide to nonconjugated, ethylenically unsaturated mononitriles having 4 to 20 carbon atoms in the presence of a zero-valent nickel catalyst promoted with an arylborane, wherein the reaction mixture thus obtained is contacted in the liquid phase with an aliphatic or alicyclic hydrocarbon after removal of sufficient mononitriles to permit the formation of two liquid phases, the improvement which comprises introducing at least about 150 ppm by weight of essentially water-free ammonia into the reaction mixture before contacting it with said hydrocarbon.

2. The process of claim 1 wherein at least about 200 ppm of ammonia is introduced.

3. The process of claim 1 wherein about 200–500 ppm of ammonia is introduced.

4. The process of claim 3 wherein the reaction mixture is maintained at a temperature of 25°–80° C.

* * * * *